US 6,551,578 B2

(12) United States Patent
Adjei et al.

(10) Patent No.: US 6,551,578 B2
(45) Date of Patent: *Apr. 22, 2003

(54) MODULATED RELEASE PARTICLES FOR AEROSOL DELIVERY

(75) Inventors: Akwete L. Adjei, Bridgewater, NJ (US); Yaping Zhu, Highland Park, NJ (US)

(73) Assignee: Aeropharm Technology Incorporated, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,556

(22) Filed: Feb. 15, 2001

(65) Prior Publication Data

US 2002/0110525 A1 Aug. 15, 2002

(51) Int. Cl.[7] .............................. A61K 9/00; A61K 9/12

(52) U.S. Cl. .................................. 424/45; 514/1; 514/2; 128/200.14

(58) Field of Search ................................ 424/45; 514/1, 514/2; 128/200.14

(56) References Cited

U.S. PATENT DOCUMENTS

| | | | |
|---|---|---|---|
| 5,843,881 A | * | 12/1998 | Dubois et al. ................. 512/1 |
| 6,136,294 A | * | 10/2000 | Adjei et al. .................... 424/45 |
| 6,261,539 B1 | * | 7/2001 | Adjei et al. .................... 424/46 |

* cited by examiner

Primary Examiner—Michael G. Hartley
Assistant Examiner—M. Haghighatian
(74) Attorney, Agent, or Firm—Frommer Lawrence & Haug LLP

(57) ABSTRACT

A modulated release aerosol formulation is disclosed. The formulation comprises a polysaccharide polymer having a selected medicament associated therewith, a fluid carrier for carrying and delivering the construct and a stabilizer.

25 Claims, 2 Drawing Sheets

Plasma Concentration Profiles of hr-Insulin following iv and Aerosol Administration
(0.1 and 5 U/kg, respectively)

Conc. of insulin in plasma (ng/ml)

Formulation I, 5u/kg, (n=5)

iv, 0.1u/kg, (n=5)

Time (min)

MODULATED RELEASE PARTICLES FOR AEROSOL DELIVERY

BACKGROUND OF THE INVENTION

1. Field of the Invention

This invention relates to modulated release aerosol particles, and more particularly, to medicinal aerosol particles comprising polymeric vesicles which entrap a selected medicament and provide slow release thereof.

2. Description of the Related Art

Many drugs currently administered by inhalation come primarily as liquid or solid aerosol particles of respirable size. For biotherapeutic drugs, this may present a problem, as many of these medicaments are unstable in aqueous environments for extended periods of time and are rapidly denatured if micronized by high shear grinding or other comminution methods when presented as dry powders. Additionally, a number of these medicaments do not survive long enough in the lung as they are extracted quickly from the lung environment after they are administered as inhalation aerosols. Significant drug loss could also occur by deactivation either as a result of reactivity of the medicament with device and container surfaces, or during aerosolization, particularly in high shear, energy intensive, nebulized systems [Mumenthaler, M, et al., *Pharm. Res.*, 11:12–20 (1994)].

To overcome these instability problems, many drug and excipient systems contain biodegradable carriers, such as poly(lactide-co-glycolides, have been developed for biotherapeutic proteins and peptides [Liu, R., et al., *Biotechnol. Bioeng.*, 37:177–184 (1991)]. These medicaments, presumably, are adequately protected in their carrier systems, and thus do not undergo as much denaturation as realized in aqueous media. Importantly, these polymers prolong drug release at the site of absorption so that the effect of the drug is also subsequently sustained in the body.

Most therapeutic peptides and proteins are poorly absorbed through biologic membranes even upon formulation with penetration enhancers, possibly due to a combination of several factors, including large molecular size (i.e., $\geq 1000$ daltons), ionization, high surface charge, enzymatic and chemical instability, and low permeability of absorption barriers in the body of a patient, e.g. human being or other animal. In numerous therapies, drug dosimetry is increased by orders of magnitude to achieve minimum systemic concentrations required for efficacy. In other cases the drug product is formulated with exotic absorption promoters in order to improve permeability across the absorption barrier. But such formulations usually present serious toxicological liabilities. The clinical and pharmaceutical chemistry sciences, in an attempt to accomplish the highest level of therapeutic benefit for these compounds, have resorted to chemical modifications as a principal mode for improving biological activity of these drugs in the body of the patient. The mode of drug administration to the body has also gradually expanded from oral and parenteral to transdermal, rectal and the pulmonary routes of administration, i.e., nose and lung. Success and achievement with these drug delivery approaches are mixed largely due to lack of acceptance of the newer, complex molecules that must be used for treating difficult diseases of the body, e.g., infections, malignancies, cardiovascular, endocrine, neurologic diseases, and a variety of immunologically compromised diseases, like AIDS.

Accordingly, what is desired and needed is a fluid propelled formulation system comprising an active pharmaceutical ingredient ("API") that is stable and protected by a rate-limiting carrier, easily manufactured, and therapeutically effective when administered as fluid dispersed particles to the lung of a patient, e.g. a human being or another animal.

SUMMARY OF THE INVENTION

This invention relates to modulated release aerosol particles, and more particularly, to medicinal, respirable aerosol particles comprising polysaccharide vesicles which are associated with, e.g. form a part of a construct with or entrap therewithin a selected medicament and provide slow release thereof.

BRIEF DESCRIPTION OF THE DRAWING

The nature of the invention will appear more fully from the following detailed description taken in conjunction with the appended drawing, in which.

DETAILED DESCRIPTION OF THE INVENTION

Figure 1:
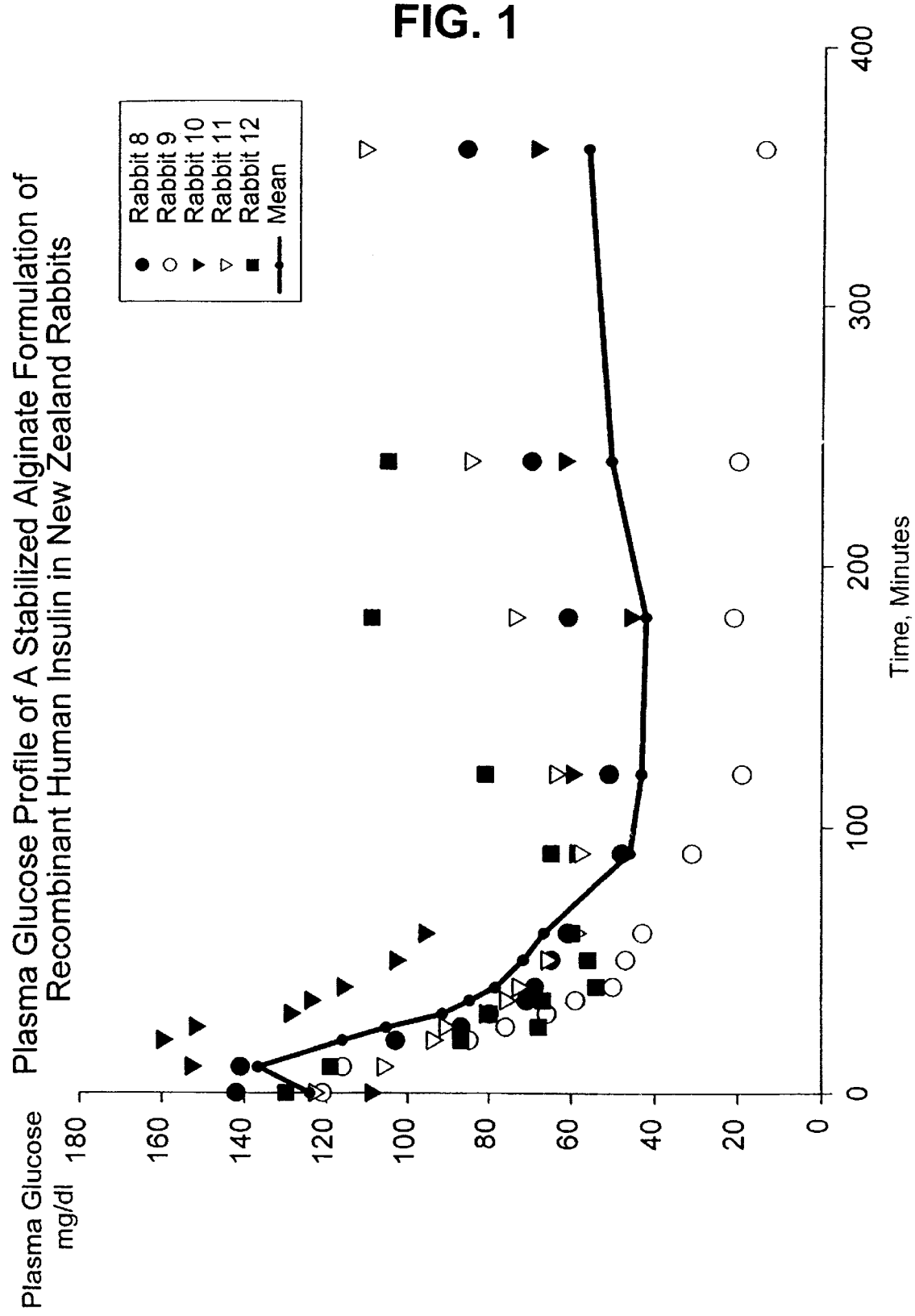
FIG. 1 is a graphical representation of a plasma glucose profile of a stabilized alginate formulation of recombinant human insulin in New Zealand rabbits.

This application makes reference to U.S. applications Ser. No. 09/158,369, filed on Sep. 22, 1998, now U.S. Pat. Nos. 6,136,294 and 09/209,228 filed on Dec. 10, 1998, which are incorporated hereinto by reference in their entirety.

This invention involves stable, modulated release, respirable, aerosolizable particles suitable for delivery of medicaments to the lung, which comprise (1) a medicament or drug, (2) a naturally occurring polysaccharide polymeric construct into which the drug is associated, i.e. is encapsulated therewithin or being part of the construct, (3) a suitable fluid or propellant, (4) a suitable stabilizer. The polysaccharide polymeric construct, modulates release of the encapsulated drug to the body of a patient, e.g. a human being or another animal, when the formulation is administered to the patient's respiratory tract.

A suitable macromolecular medicament or drug is one which is suitable for administration by inhalation, the inhalation being used for oral and nasal inhalation therapy. A stable, colloidal dispersion of a medicament in a fluid, e.g. air, hydrocarbon gases, chlorofluorocarbon (CFC) propellants or non-CFC propellants, such as tetrafluoroethane (HFA-134a) and heptafluoropropane (HFA-227), is described.

A stabilizer of a polyionic species, such as an amino acid and a small molecule peptide, as an inactive formulation component, which triggers loss of adhesive bond strength between the medicament particles, may optionally be employed. An electret or sterially stabilized aerocolloid particles of the selected medicaments is thus formed. An electret is the electrostatic equivalent of a permanent magnet but can be susceptible to breakdown in the presence of moisture, such as that present in air or at ambient humidity conditions of the respiratory tract. Accordingly the present invention applies to particles formulated for use in dry powder aerosols, portable nebulizer systems, as well pressurized metered dose inhaler formulations.

The resultant aerocolloid is chemically and physically stable and can remain in suspension until the selected medicament or drug particles reach the alveolar or other absorption sites in the airways of a patient, e.g. human, other animal, being treated. Once at the absorption site, the drug particles should be efficiently trapped at the deposition site as a result of moisture in the ambient, dissolve rapidly in the epithelial lining fluids, and be absorbed quickly across the biomembranes of the patient, thereby limiting possible deactivation by metabolizing enzymes in the airways.

As used herein the following terms are defined as follows.

The term "rate of release" from the polysaccharide polymer medicament carrier is defined as the amount of medicament released per unit time either to the lung environment or from the lung environment to the systemic circulation of the body of the patient treated.

The terms "peptide", "polypeptide", "oligopeptide" and "protein" shall be used interchangeably when referring to peptide or protein drugs and shall not be limited as to any particular molecular weight, peptide sequence or length, field of bioactivity or therapeutic use unless specifically stated.

A suitable medicament to which the subject invention is directed includes a peptide, polypeptide, or protein biotherapeutic medicament ranging from 0.5 K Dalton to 150 K Dalton in molecular size. In particular, the peptide, polypeptide, or protein biotherapeutic medicament includes diabetic aids; such as insulins and insulin analogs; amylin; glucagon; surfactants; immunomodulating peptides such as cytokines, chemokines, lymphokines; interleukins, such as taxol, interleukin-1, interleukin-2, and interferons; erythropoetins; thrombolytics and heparins; anti-proteases, antitrypsins and amiloride; rhDNase; antibiotics and other anti-infectives; hormones; and growth factors, such as parathyroid hormones, LH-RH and GnRH analogs; nucleic acids; DDAVP; calcitonins; cyclosporine; ribavirin; enzymes; heparins; hematopoietic factors; cyclosporins; vaccines; immunoglobulins; vasoactive peptides; antisense agents; genes, oligonucleotide, and nucleotide analogs.

The term "diabetic aid" includes natural, synthetic, semi-synthetic and recombinant medicaments such as activin, glucagon, insulin, somatostatin, proinsulin, amylin, and the like.

The term "insulin" shall be interpreted to encompass insulin analogs, natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog", "monomeric insulin" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which act as insulin in decreasing blood glucose levels. In general, the term "insulin analogs" of the present invention include "insulin lispro analogs", as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

The term "amylin" includes natural human amylin, bovine, porcine, rat, rabbit amylin, as well as synthetic, semi-synthetic or recombinant amylin or amylin analogs including pramlintide and other amylin agonists, as disclosed in U.S. Pat. Nos. 5,686,411 and 5,854,215, both of which are incorporated hereinto by reference in their entirety.

The term "immunomodulating proteins" include cytokines, chemokines, lymphokines complement components, immune system accessory and adhesion molecules and their receptors of human or non-human animal specificity. Useful examples include GM-CSF, IL-2, IL-12, OX40, OX40L (gp34), lymphotactin, CD40, CD40L. Useful examples include interleukins, for example interleukins 1 to 15; interferons alpha, beta or gamma; tumour necrosis factor, granulocyte-macrophage colony stimulating factor (GM-CSF), macrophage colony stimulating factor (M-CSF), granulocyte colony stimulating factor (G-CSF), chemokines, such as neutrophil activating protein (NAP); macrophage chemoattractant and activating factor (MCAF), RANTES, macrophage inflammatory peptides MIP-1a and MIP-1b, complement components and their receptors, or an accessory molecule, such as B7.1, B7.2, ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented, for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can, for example, comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular origin and antigenicity, namely, alpha-interferon (leukocytes), beta-interferon (fibroblasts) and gamma-interferon (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. Reference is made to Viscomi, 1996 Biotherapy 10:59–86, the contents of which are incorporated by reference hereinto in its entirety. The terms "alpha.-interferon", "alpha interferon", "interferon alpha", "human leukocyte interferon" and "IFN" are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acid sequences. Purified natural human alpha inteferons and mixtures thereof which may be used in the practice of the invention include but are not limited to Sumiferon RTM interferon alpha-n1 available from Sumitomo, Japan; Welfferong interferon alpha-n1 (Ins) available from Glaxo-Wellcome Ltd., London, Great Britain; and Alferon RTM interferon alpha-n3 available from the Purdue Frederick Co., Norwalk, Conn.

The term "erythropoietin" applies to synthetic, semi-synthetic, recombinant, natural, human, monkey, or other animal or microbiological isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eucaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) cells may be further characterized by freedom from association with human proteins or other contaminants which may be associated with erythropoietin in its natural mammalian cellular environment or in extracellular fluids such as plasma or urine. The products of typical yeast (e.g., *Saccaromyces cerevisiae*) or procaryote (e.g., *E. coli*) host cells are free of association with any mammalian proteins. Depending upon the host employed, polypeptides of the invention may be glycosylated with mammalian or other eucaryotic carbohydrates or may be nonglycosylated. Polypeptides of the invention may also include an initial methionine amino acid residue (at position −1). Novel glycoprotein products of the invention include those having a primary structural conformation such as growth hormone, thyroid hormone, thyroid releasing hormone (TRH), gonadotropin-releasing hormone (GnRH), leuteininzing hormone, leuteininzing hormone-releasing hormone (LHRH, including the superagonists and antagonists, such as leuprolide, deltirelix, gosorelin, nafarelin, danazol, etc.) sourced from natural, human, porcine, bovine, ovine, synthetic, semi-synthetic, or recombinant sources. These also include somatostatin analogs such as octreotide (Sandostatin). Other agents in this category of biotherapeutics include medicaments for uterine contraction (e.g., oxytocin), diuresis (e.g., vasopressin), neutropenia (e.g., GCSF), medicaments for respiratory disorders (e.g., superoxide dismutase), RDS (e.g., surfactants, optionally including apoproteins), and the like.

The term "enzymes" include recombinant deoxyribonuclease such as DNAse (Genentech) proteases (e.g., serine proteases such as trypsin and thrombin), polymerases (e.g., RNA polymerases, DNA polymerases), reverse transcriptases and kinases, enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

The terms "heparins" and "thrombolytics" include anti-clotting factors such as heparin, low molecular weight heparin, tissue plasminogen activator (TPA), urokinase (Abbokinase) and other factors used to control clots.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). Also included are antibodies which recognize self-antigens, such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, thyroid releasing hormone (TRH), gonadotropin-releasing hormone (GnRH), leuteininzing hormone, leuteininzing hormone-releasing hormone (LHRH, including the superagonists and antagonists, such as leuprolide, deltirelix, gosorelin, nafarelin, danazol, etc.) sourced from natural, human, porcine, bovine, ovine, synthetic, semi-synthetic or recombinant sources. These also include somatostatin analogs such as octreotide (Sandostatin). Other agents in this category of biotherapeutics include medicaments for uterine contraction (e.g., oxytocin), diuresis (e.g., vasopressin), neutropenia (e.g., GCSF), medicaments for respiratory disorders (e.g., superoxide dismutase), RDS (e.g., surfactants, optionally including apoproteins), and the like.

The term "enzymes" include recombinant deoxyribonuclease such as DNAse (Genentech) proteases (e.g., serine proteases such as trypsin and thrombin), polymerases (e.g., RNA polymerases, DNA polymerases), reverse transcriptases and kinases, enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized and selected and combined in accordance with the invention include, but are not limited to, agonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

The term "analog" refers to a molecule, which shares a common functional activity with the molecule to which it is deemed to be comparable and typically shares common structural features as well.

The term "recombinant" refers to any type of cloned biotherapeutic expressed in procaryotic cells or a genetically engineered molecule, or combinatorial library of molecules which may be further processed into another state to form a second combinatorial library, especially molecules that contain protecting groups which enhance the physicochemical, pharmacological, and clinical safety of the biotherapeutic agent.

The term "vaccines" refers to therapeutic compositions for stimulating humoral and cellular immune responses, either isolated, or through an antigen presenting cell, such as an activated dendritic cell, that is able to activate T-cells to produce a multivalent cellular immune response against a selected antigen. The potent antigen presenting cell is stimulated by exposing the cell in vitro to a polypeptide complex. The polypeptide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still other preferred embodiments, the polypeptide antigen may be any one of the oncogene product peptide antigens. The polypeptide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p22RAS, and p53; however, other embodiments, such as viral antigens, are also within the scope of the invention.

The term "mmunoglobulins" encompasses polypeptide oligonucleotides involved in host defense mechanisms, such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

For purposes of the formulations of this invention, which are intended for inhalation into the lungs, the biotherapeutic medicament is associated with the naturally occurring polysaccharide polymer to which it is destined to be combined. By "associate" or "associated" is meant that the medicament is present as a matrix or a part of a polymeric construct along with the polysaccharide polymer or is encapsulated as a microsphere in a polysaccharide polymer or in polysaccharide polymeric construct particle, or is on a surface of such particle, whereby a therapeutically effective amount or fraction (e.g., 95% percent or more) of the biotherapeutic is particulate. Typically, the construct particles have a diameter of less than about 10 microns, and preferably less than about 5 microns, in order that the particles can be inhaled into the respiratory tract and/or lungs of the patient being treated, e.g. a human or other animal.

A suitable polymeric construct is selected. Such a construct is one which will incorporate therein or encapsulate the selected medicament, e.g. insulin, amylin, octreotide, erythopoietin, immunoglobulin, leuprolide, glucagon and provide a controlled or modulated release of the medicament therefrom to the sites of action or application of the patient's body, e.g. from the lung to the local surrounding environment of the human being or other animal.

A suitable polysaccharide is a polymer selected from the group of an alginate salt, e.g. $Li^+$, $Na^+$, $K^+$, $Ca^{++}$, $NH^{+++}$, $NH^{++++}$ etc., such as sodium alginate, calcium alginate, sodium-calcium alginate, ammonium alginate, sodium-ammonium alginate, or calcium-ammonium alginate. A preferred aliginate modulating releasing agent is ammonium calcium alginate. These materials are typically used in injectable implants and microsphere preparations for controlled release. A commercial form of ammonium calcium alginate is Keltose, manufactured and distributed by ISP (International Specialty Products, 1361 Alps Road, Wayne, N.J. 07470). As used herein, "alginate" means alginic acid, or any of its salts; or other naturally occuring polysaccharide or carbohydrate based polymers such as gum arabic, pectin, galacturonic acid, gum karaya; gum Benjamin, plantago ovata gum; agar; carrageenan; cellulose; gelatin; or a mixture of any of the foregoing polymers.

Alginates are pharmaceutical excipients generally regarded as safe and used therefore to prepare a variety of pharmaceutical systems well documented in the patent literature [S. Bloor, U.S. Pat. No. 6,166,084; Ikeda, et al., U.S. Pat. No. 6,166,043; Ikeda, et al., U.S. Pat. No. 6,166,042; Fassler, et al., U.S. Pat. No. 6,166,004; Itakura, et al., U.S. Pat. No. 6,165,615;].

Alginates are naturally occurring polymers comprising polysaccharide chains. These polymers have the propensity to absorb water thus swelling to become gel-like structures in solution. Upon inhalation of the resultant core formulation by a patient being treated, the gel dissolves in the body of such patient, thus releasing its drug payloads in a dissolution controlled manner. Such a polymer system forms a construct or a matrix when formed in situ with the selected medicament or medicaments whereby such medicament or medicaments forms part of the matrix or is encapsulated within the matrix. Upon such formation or encapsulation, the medicament, e.g. entrapped insulin, is time-released or modulated from the site of action in the body, e.g. the lungs, the respiratory tract, node, ear, etc., to the surrounding environment or tissues of the body of the patient treated.

The polysaccharide polymer, e.g. an alginate salt, is typically present in the resultant controlled-release formulation in an amount ranging from about 0.000001% to about 10% by weight of the total weight of the formulation.

The biotherapeutic medicament is present in the inventive polymer construct in a therapeutically effective amount, that is, an amount such that the biotherapeutic medicament can be incorporated into an aerosol formulation such as a dispersion aerosol, via oral or nasal inhalation, and cause its desired therapeutic effect, typically preferred with one dose, or through several doses.

The term "dosing period" shall be interpreted to mean the period during which administration of the selected medicament may be given to a patient in need thereof by the intrapulmonary route of administration which period may encompass preferably one or more hours in a day or a few days to several weeks but less preferably over a month or under 1 hour, but during which period multiple inhalations are made by the patient and multiple doses of the selected medicament are released and inhaled.

The term "amount" as used herein refers to a quantity or to a concentration as appropriate to the context. The amount of a drug that constitutes a therapeutically effective amount varies according to factors such as the potency of the particular biotherapeutic medicament, the route of administration of the formulation, and the mechanical system used to administer the formulation. A therapeutically effective amount of a particular drug can be selected by those of ordinary skill in the art with due consideration of such factors. Generally a therapeutically effective amount of biotherapeutic medicament will be from about 0.00001 parts by weight to about 5 parts by weight based on 100 parts by weight of the fluid or propellant selected.

A suitable fluid includes air, a hydrocarbon such as n-butane, propane, isopentane, etc. or a propellant. A suitable propellant is any fluorocarbon, e.g. a 1–6 hydrogen containing flurocarbon (such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as propellants 11, 12 and 114 or a mixture thereof. Non-CFC propellants such as 1,1,1,2-tetrafluoroethane (Propellant 134a), 1,1,1,2,3,3,3-heptafluoropropane (Propellant 227) or a mixture thereof are preferred. The fluid or propellant is preferably present in an amount sufficient to propel a plurality of selected doses of drug from an aerosol canister when such is employed.

A suitable first stabilizer is selected. A suitable first stabilizer includes (1) an amino acid selected from the group consisting of (a) a monoamino carboxylic acid of the formula, $H_2N—R—COOH$(I), (b) a monoamino dicarboxylic acid of the formula, $H_2N—R(COOH)_2$ (II) and (c) a diamino monocarboxylic acid of the formula $(H_2N)_2—R$ COOH (III), where R is a straight or branched alkyl radical of from 1 to 22 carbon atoms, which can be mono or poly-substituted with sulfide (—S—), oxide (—O—), hydroxyl (—OH), amide (—NH), sulfate (—SO4); aryl of the formula $$\underset{}{\bigodot}-X,$$

where X is hydrogen, halogen alkyl of 1 to 6 carbon atoms, alkoxy of 1 to 6 carbon atoms, hydroxy and nitro; and heterocyclic, selected from the groups consisting of thienyl, furyl, pyranyl, imidazolyl, pyrrolyl, thizolyl, oxazolyl, pyridyl, and pyrimidinyl; (2) a derivative of the amino acid selected from (a) an acid addition salt of the amino group, as well as (c) an ester of the carboxylic acid group obtained from aliphatic straight or branched chain alcohols of from 1 to 6 carbon atoms, (3) an ether of any of the foregoing; (4) a hydrate or semi-hydrate of any of the foregoing and (5) a mixture of the amino acid and the derivative of the amino acid.

Suitable amino acids of the inventive formula include glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula II include aspartic acid, and glutamic acid, compounds of the formula (III) include arginine, glutamine, lysine, hydroxylysine, ornithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about 15 seconds to about 15 minutes after agitation.

For optimal functional and therapeutic performance of the aerosol formulation, as an aerosol suspension, the stabilizer e.g., amino acid stabilizer, is present either as a coarse carrier (e.g., 20–90 $\mu$m) or as a finely micronized powder, $\leq 10\,\mu$m in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

Alternatively, a second suitable stabilizer is selected. A second suitable stabilizer is a "water addition." As used herein, a "water addition" is an amount of water which (1) is added, either initially with other components of the described aerosol formulation, e.g. medicament associated with the polymeric construct as part thereof or encapsulated therein, and fluid carrier, or after the other components, e.g. medicament, fluid carrier are combined and processed, (2) is in addition to the water which is always present and which develops during processing and/or storage of the aerosol formulation, i.e. "developed" or "nascent" formulation water, and (3) is present in an amount which further stabilizes a medicinal aerosol formulation, e.g. rosiglitazone maleate, having nascent formulation water.

An aerosol formulation preferably comprises the water addition in an amount effective to more effectively stabilize the formulation relative to an identical formulation not containing the water addition, i.e. containing only nascent formulation water, such that the drug e.g., an insulin containing construct, does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

It is of course understood, that the first stabilizer can be combined with the second stabilizer in an approximate combined concentration, e.g. typically to 300 ppm to 2000 ppm, to achieve the desired stability of the resultant formulation.

The particular amount of stabilizer e.g. amino acid stabilizer alone or water of addition stabilizer alone or both stabilizers combined, that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.001 parts per million to about 200,000 parts per million, more preferably about 1 part per million to about 10,000 parts per million, most preferably from about 10 parts per million to about 5,000 parts per million of the total formulation.

It has surprisingly been found that the formulation of the invention, e.g. suspension or solution is stable without the necessity of employing a cosolvent, such as ethanol, or surfactants. However, further components, such as conventional lubricants or surfactants, co-solvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

Generally the formulations of the invention can be prepared by combining, matrixing, or encapsulating (i) the biotherapeutic medicament or drug with a sufficient amount of the modulating polymer in an amount sufficient to provide a plurality of therapeutically effective doses of the biotherapeutic; (ii) if necessary, combining or adding an appropriate suspension stabilizer in an amount effective to stabilize each of the formulations; and (iii) dispersing the matrixed or encapsulated and stabilized biotherapeutic medicament in an appropriate fluid or propellant in an amount sufficient to propel a plurality of doses, e.g. from an aerosol canister.

A sufficient amount of the modulating polymer, e.g. an alginate, is dependent upon the desired rate of release of the medicament itself. Typically, for a release of about 2 to about 6 hours, the concentration of the polymeric material ranges from about 10 ppm to about 100,000 ppm to effect a desired release profile e.g. about 15 minutes to about 12 hours.

Particles of the selected polysaccharide polymer system may be prepared using solutions or emulsion preparations of the polymer and active pharmaceutical ingredient which may subsequently be dried either by the use of an antisolvent such as carbon dioxide, nitrogen, or any other appropriate antisolvent, or by solvent evaporation, spray drying, solvent extraction, phase separation, coacervation, interfacial polymerization, and other methods well known to those of ordinary skill in the art. Polysaccharide polymeric particles may be made also using microencapsulation, by nanoparticle technology, by coating methods such as spray congealing, by supercritical fluid technology, or by micellar solubilization where various techniques known to those skilled in the art may be used. These methods are described in the following non-exhaustive list of references which are incorporated hereinto by reference:

(1) Doubrow, M., Ed., "Microcapsules and Nanoparticles in Medicine and Pharmacy," CRC Press, Boca Raton, 1992.
(2) Benita et al., J. Pharm. Sci. 73, 1721–1724 (1984);
(3) Cook et al., U.S. Pat. No. 4,044,126;
(4) Cook et al., U.S. Pat. No. 4,363,923;
(5) Cook et al., U.S. Pat. No. 4,414,209;
(6) Ecanow, U.S. Pat. No. 4,963,367;
(7) Hallworth et al., U.S. Pat. No. 4,206,758;
(8) Hallworth et al., U.S. Pat. No. 4,353,365;
(9) Lindsay, U.S. Pat. No. 5,169,433;
(10) Makiej, Jr., U.S. Pat. No. 5,002,048;
(11) Mathiowitz and Langer, J. Controlled Release 5,13–22 (1987);
(12) Mathiowitz et al., Reactive Polymers 6, 275–283 (1987);
(13) Mathiowitz et al., J. Appl. Polymer Sci. 35, 755–774 (1988);
(14) Mathiowitz et al., Scanning Microscopy 4: 329–340 (1990);
(15) Mathiowitz et al., J. Appl. Polymer Sci. 45, 125–134 (1992);
(16) Martin, U.S. Pat. No. 4,892,232;
(17) Newell et al., U.S. Pat. No. 4,811,731;
(18) Newell et al., U.S. Pat. No. 4,627,432;
(19) Ray, U.S. Pat. No. 4,800,903;
(20) Riccio, U.S. Pat. No. 3,856,185;
(21) Ronge, U.S. Pat. No. 5,056,511;
(22) Sievers et al., U.S. Pat. No. 4,970,093;
(23) Smith, U.S. Pat. No. 4,582,731;
(24) Whitsett, U.S. Pat. No. 5,013,720; and
(25) McNab, U.S. Pat. No. , 5,044,523.
(26) Hanna and York, World Intellectual Property Organization Patent Number WO9959710A1
(27) Hanna, et al., World Intellectual Property Organization Patent Number WO9944733A1
(28) Hanna and York, World Intellectual Property Organization Patent Number WO9836825A1

The modulated release particles of the invention can be delivered to the respiratory tract and/or lung of the patient to be treated, e.g. a human being or other animal, by oral inhalation in order to effect bronchodilation or in order to treat a condition susceptible of treatment by inhalation, e.g., asthma, chronic obstructive pulmonary disease.

The modulated release particles of the invention can also be delivered to the lung in order for the biotherapeutic agent to be delivered at measured rates to the systemic circulation for treatment of diseases elsewhere in the body, e.g., diabetes, hormone replacement, cancer, erythropoiesis, infection, or for immune protection such as achievable with vaccines.

The modulated release particles of the invention can also be delivered by nasal inhalation in order to treat, for example, allergic rhinitis, rhinitis, (local) or diabetes (systemic), or they can be delivered via topical (e.g., buccal) administration in order to treat, e.g., angina or local infection.

Figure 2:
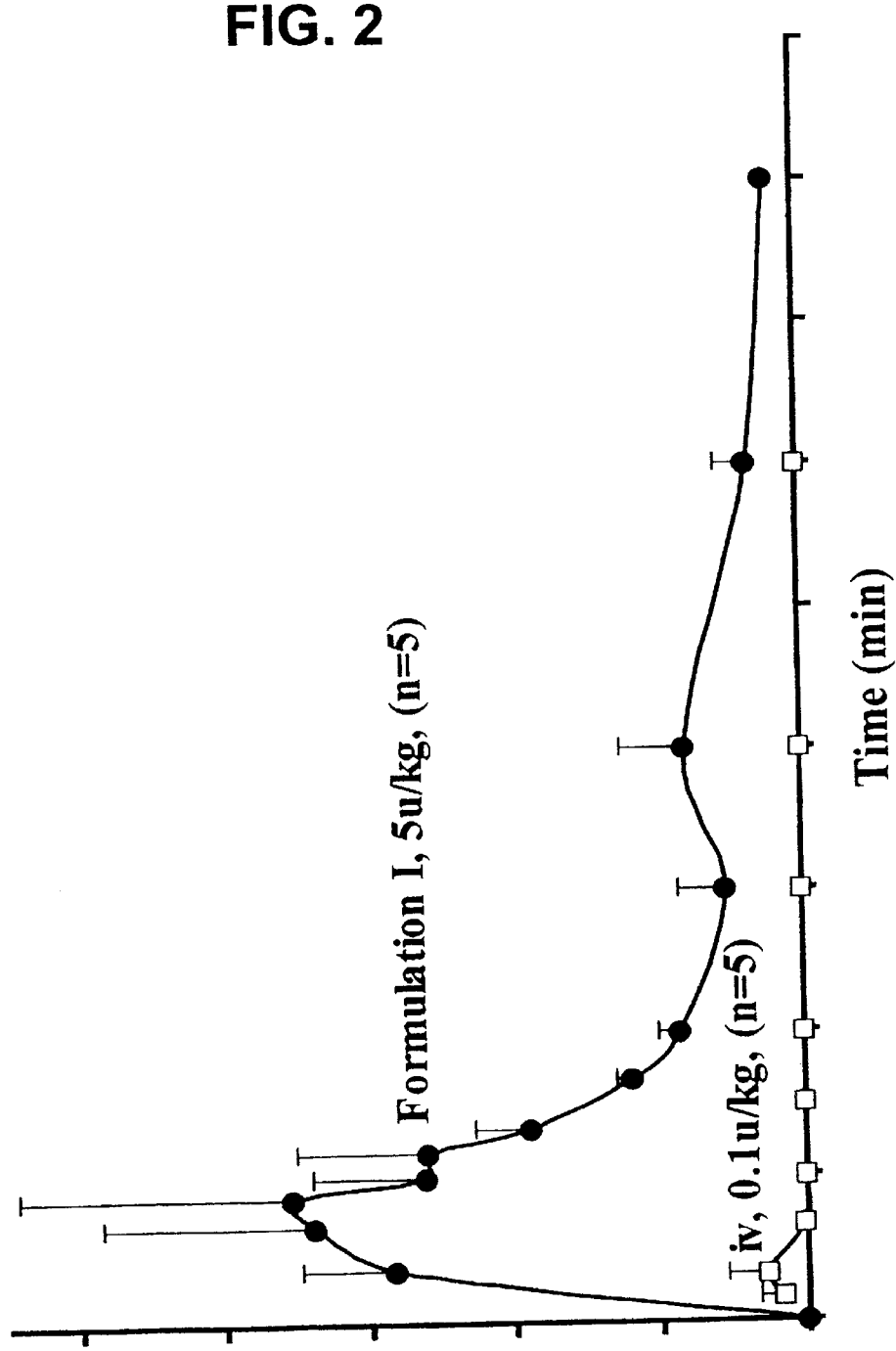
FIG. 2 is a graphical representation of a plasma concentration profile of hr-insulin following intravenous and aerosol administration according to the invention.

Depending upon the concentration of the polymer, e.g. alginate, drug release rates range from about 5 minutes to several hours. Examples of the release profile, and the corresponding glycemic control relative to an intravenous administration in New Zealand rabbits is given in FIGS. 1 and 2.

We claim:

1. A modulated release aerosol formulation, which consists essentially of, a. polymeric construct comprising a polysaccharide polymer having a selected medicament associated therewith; and
   b. fluid carrier for carrying and delivering said construct; and
   c. a stabilizer selected from the group consisting of a first stabilizer, a second stabilizer and a mixture of the foregoing stabilizers.

2. A modulated release aerosol formulation, which consists essentially of, a. selected particulate medicament;
b. particles of a polysaccharide polymer having said medicament associated therewith;
c. a stabilizer selected from the group consisting of a first stabilizer, a second stabilizer and a mixture of the foregoing stabilizers combined with said particles; and
d. a fluid carrier for carrying and transporting said combined particles.

3. The formulation as defined in claim 1 wherein said stabilizer is a water of addition.

4. The formulation as defined in claim 1 wherein said stabilizer is said first stabilizer selected from the group consisting of (1) an amino acid selected from the group consisting of (a) a monoamino carboxylic acid of the formula, H$_2$N—R—COOH(I), (b) a monoamino dicarboxylic acid of the formula, H$_2$N—R(COOH)$_2$ (II) and (c) a diamino monocarboxylic acid of the formula (H$_2$N)$_2$—R COOH (III), where R is a straight or branched alkyl radical of from 1 to 22 carbon atoms, which can be mono or poly-substituted with sulfide (—S—), oxide (—O—), hydroxyl (—OH), amide (—NH), sulfate (—SO$_4$); aryl of the formula

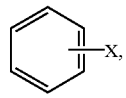

where X is hydrogen, halogen, alkyl of 1 to 6 carbon atoms, alkoxy of 1 to 6 carbon atoms, hydroxy and nitro; and heterocyclic selected from the group consisting of thienyl, furyl, pyranyl, imidazolyl, pyrrolyl, thizolyl, oxazolyl, pyridyl, and pyrimidinyl; (2) a derivative of the amino acid selected from (a) an acid addition salt of the amino group, (b) an amide of the carboxylic acid group, (c) an ester of the carboxylic acid group obtained from aliphatic straight or branched chain alcohols of from 1 to 6 carbon atoms, (3) an ether of any of the foregoing; (4) a hydrate or semi-hydrate of any of the foregoing and (5) a mixture of the amino acid and the derivative of the amino acid.

5. The formulation as defined in claim 1 wherein said first stabilizer is an amino acid selected from the group consisting of the twenty existing amino acids.

6. The formulation as defined in claim 1 wherein said polymer is selected from the group consisting of alginic acid or a pharmaceutically acceptable salt thereof; guar gum; gum karaya; gum Benjamin, plantago ovata gum; agar; carrageenan; cellulose; galaturonic acid or a mixture of any of the foregoing polymers.

7. The formulation as defined in claim 1 wherein said medicament is a protein or peptide medicament having a molecular size ranging from about 1K Dalton to about 150 K Daltons.

8. The formulation as defined in claim 7 wherein said medicament is selected from the group consisting of an insulin, an insulin analog, an amylin, an immunodilating protein, an interleukin, an inteferon, an erythropoietan, a heparin, a thrombolytic, an antitrypsin, an antiprotease, a hormone, a growth factor, an enzyme, a nucleic acid, an immunoglobulin, an antibiotic, an antiinfective, a calcitonin, a hematopoietic factor, a vaccine, a vasoactive peptide, an antisense agent, an oligonucleotide, DNase, a cyclosporin, ribavirin or a mixture of any of the foregoing medicaments.

9. The formulation as defined in claim 7 wherein said medicament is selected from the group consisting of an insulin, an insulin analog, an amylin, glucagon, LH-RH, deltirex, leuprolide, gosorelin, nafarelin, octreotide, somatostatin, a calcitonin, parathyroid hormone, TRH, growth hormone-releasing hormone, G-CSF, G-SF, a cytokine, rhDNAse, a heparin, an oligoneucleotide, ribavirin, glucagon, acetohexamide, chlorpropamide, tolazemide, tolbutamide, glipizide, glyburide, metformin, phentolamine, tumor neurosis factor (TNF), nerve growth factor (NGF), macrophage-colony stimulating factor (M-CSF), heparinase, bone morphogenic protein (BMP), hANP, glucagon-like peptide (GLP-1), renin, bradykinin, a bacitracin, a polymyxin, a colistin, tyrocidine, a gramicidin, a monoclonal antibody, a vaccine or a mixture of any of the foregoing medicaments.

10. The formulation as defined in claim 6 wherein said polymer is present in an amount of about 0.000001 to about 10 percent by weight of the total weight of the formulation.

11. The formulation as defined in claim 1 wherein said fluid carrier is selected from the group of propellants consisting of 1,1,1,2-tetrafluoethane, 1,1,1,2,3,3,3-heptafluoropropane or a mixture thereof.

12. The formulation as defined in claim 1 wherein said fluid carrier is a compressed gas selected from the group consisting of air, carbon dioxide, nitrogen and a mixture of any of the foregoing compressed gases.

13. The formulation as defined in claim 1 wherein said fluid carrier is a hydrocarbon selected from the group consisting of n-butane, propane, isopentene and a mixture of any of the foregoing hydrocarbons.

14. The formulation as defined in claim 1 wherein said fluid carrier is a chlorofluorocarbon selected from the group consisting of propellant 11, propellant 12, propellant 114 and a mixture of any of the foregoing propellants.

15. The formulation as defined in claim 1 wherein said stabilizer is present in an amount ranging from about 300 parts by weight to about 2000 parts by weight to the total weight of the formulation.

16. A method of preparing a stable medicinal aerosol formulation according to claim 1, which comprises, a. combining said selected medicament with said polymer to form said polymeric construct, wherein said medicament is associated with said polymer in an amount sufficient to provide a plurality of therapeutically effective doses;

b. combining said stabilizer with said construct to form a stabilizer combined construct;

c. combining said construct with a fluid carrier, where said carrier is present in an amount sufficient to transport and deliver a plurality of said therapeutically effective doses, to form a mixture; and d. dispersing said mixture.

17. A method of treating in a human being or another animal a condition capable of treatment by oral or nasal inhalation, which comprises;

administering a formulation according to claim 1 to said human being or animal by oral or nasal inhalation.

18. A formulation according to claim 1 in an aerosol canister equipped with a metered dose valve.

19. A metered dose inhaler containing a modulated release medicinal formulation, the formulation consisting essentially of, a. a particulate medicament in a therapeutically effective amount;

b. a polysaccharide polymer with which said particulate medicament is associated to form a particulate polymeric construct;

c. a fluid carrier for containing and transporting said particulate polymeric construct; and d. a suitable stabilizer selected from the group consisting of a first stabilizer, a second stabilizer and a mixture of the foregoing stabilizers present in an amount sufficient to stabilize the formulation to prevent settling, creaming or flocculation thereof for a time sufficient to allow reproducible dosing of said associated medicament after agitation of the formulation.

20. The inhaler as defined in claim 19 wherein said stabilizer is selected from the group consisting of the twenty existing amino acids, any mixture thereof and any derivative of the foregoing.

21. The inhaler as defined in claim 20 wherein said stabilizer is selected from the group consisting of (1) a di-peptide selected from a salt and an ester of oxidized and unoxidized L-cysteinylglycine, gamma-L-glutamyl-L-cysteine, N-acetyl-L-cystein-glycine; (2) a conjugated, unconjugated or polymeric form of L-Gly-L-glu and L-Val-L-Thr; (3) L-aspartyl-L-phenylamine; (4) a muramyl dipeptide; (5) a nutrient selected from L-tyrosyl-L-tyrosine, L-alanyl-L-tyrosine, L-arginyl-L-tyrosine, L-tyrosyl-L-arginin, N-Clz-L-Liu-OCH and salts and esters of the foregoing; (6) glycyl-glycine; (7) N-acetyl-L-aspartate-L-glytamate (NAAG); (8) a tripeptide selected from an oxidized and an unoxidized form of gamma-L-glutamyl-L-cysteine glycine or a muramyl tripeptide and (9) a mixture of any of the foregoing stabilizers.

22. The inhaler as defined in claim 19 wherein said stabilizer is the second stabilizer which is a water of addition.

23. The formulation as defined in claim 5 wherein said stabilizer is selected from the group consisting of (1) a di-peptide selected from a salt and an ester of oxidized and unoxidized L-cysteinylglycine, gamma-L-glutamyl-L-cysteine, N-acetyl-L-cystein-glycine; (2) a conjugated, unconjugated or polymeric form of L-Gly-L-glu and L-Val-L-Thr; (3) L-aspartyl-L-phenylamine; (4) a muramyl dipeptide; (5) a nutrient selected from L-tyrosyl-L-tyrosine, L-alanyl-L-tyrosine, L-arginyl-L-tyrosine, L-tyrosyl-L-arginin, N-Clz-L-Liu-OCH and salts and esters of the foregoing; (6) glycyl-glycine; (7) N-acetyl-L-aspartate-L-glytamate (NAAG); (8) a tripeptide selected from an oxidized and an unoxidized form of gamma-L-glutamyl-L-cysteine glycine or a muramyl tripeptide and (9) a mixture of any of the foregoing stabilizers.

24. A modulated release aerosol formulation, which consists essentially of:

a. a selected particulate medicament;

b. particles of a polysaccharide polymer selected from the group consisting of an alginic acid or a pharmaceutically acceptable salt thereof; guar gum; gum Karaya; gum Benjamin; plantago ovata gum; agar; carrageenan; cellulose; galaturonic acid or a mixture of any of the foregoing polymers having said medicament associated therewith;

c. a fluid carrier for carrying and transporting said particles of polymer;

d. a stabilizer selected from the group consisting of (1) a first stabilizer selected from the group consisting of (a) an amino acid, (b) a derivative thereof and (c) a mixture of the foregoing: and (2) a second stabilizer of a water of addition and (3) a mixture of (1) and (2); and e. cosolvent.

25. The formulation as defined in claim 24 wherein said cosolvent is ethanol.

* * * * *